(12) United States Patent
Scheel-Krüger et al.

(10) Patent No.: US 7,459,464 B2
(45) Date of Patent: Dec. 2, 2008

(54) TRIPLE MONOAMINE REUPTAKE INHIBITORS FOR THE TREATMENT OF CHRONIC PAIN

(75) Inventors: Jørgen Scheel-Krüger, Ballerup (DK); Gordon John Blackburn-Munro, Ballerup (DK)

(73) Assignee: Neurosearch A/S, Ballerup (DK)

( * ) Notice: Subject to any disclaimer, the term of this patent is extended or adjusted under 35 U.S.C. 154(b) by 19 days.

(21) Appl. No.: 10/515,275

(22) PCT Filed: May 27, 2003

(86) PCT No.: PCT/DK03/00352

§ 371 (c)(1),
(2), (4) Date: Nov. 22, 2004

(87) PCT Pub. No.: WO03/101453

PCT Pub. Date: Dec. 11, 2003

(65) Prior Publication Data

US 2005/0239824 A1    Oct. 27, 2005

(30) Foreign Application Priority Data

May 30, 2002    (DK) ............................... 2002 00832

(51) Int. Cl.
*A61K 31/46*    (2006.01)

(52) U.S. Cl. ..................................................... 514/304

(58) Field of Classification Search ................... 514/304
See application file for complete search history.

(56) References Cited

U.S. PATENT DOCUMENTS

| 4,789,673 A | 12/1988 | Stadler et al. | |
|---|---|---|---|
| 6,395,748 B2 * | 5/2002 | Scheel-Kruger et al. | 514/304 |
| 6,803,387 B1 * | 10/2004 | Mendel et al. | 514/646 |
| 2002/0061910 A1 * | 5/2002 | Wong et al. | 514/320 |
| 2002/0187958 A1 * | 12/2002 | Horrobin et al. | 514/52 |

FOREIGN PATENT DOCUMENTS

| WO | WO-97/30997 A | 8/1997 |
|---|---|---|
| WO | WO-02/094827 A | 11/2002 |
| WO | 02/102801 | * 12/2002 |

OTHER PUBLICATIONS

Yamamoto & Nozaki-Taguchi, Analysis of the Effects of Cyclooxygenase (XOX)-1 and COX-2 in Spinal Nocicptive Transmission using Indomethacin, Brain Research 739:104-110 (1996).*
Malmquist, Depression and Homicidal Violence, Int. J. of Law and Pysch., 18(2):145-162 (1995).*
Stedman's Medical Dictionary, 27th Edition, definition of Chronic.*
http://atoz.iqhealth.com, Chronic Pain.*
Priest & Hoggart, Chronic Pain: Mechanisms and Treatment, Current Opinion in Pharmacology, 2:310-315 (2002).*
Burkey et al., "Dopamine reuptake inhibition in the rostral agranular insular cortex produces antinociception", The Journal of Neuroscience, May 15, 1999, vol. 19, No. 10, pp. 4169-4179.

* cited by examiner

*Primary Examiner*—Patricia L Morris
(74) *Attorney, Agent, or Firm*—Birch, Stewart, Kolasch & Birch, LLP

(57) ABSTRACT

The present invention relates to the use of triple monoamine reuptake inhibitors for the treatment of chronic pain.

6 Claims, No Drawings

TRIPLE MONOAMINE REUPTAKE INHIBITORS FOR THE TREATMENT OF CHRONIC PAIN

TECHNICAL FIELD

The present invention relates to the use of triple monoamine reuptake inhibitors for the treatment of chronic pain.

BACKGROUND ART

Chronic pain conditions are debilitating diseases affecting at least 5-10 percent of the population at some point in their lives. For the patient suffering from a chronic pain disease, disturbance of, or disruption to their daily life is almost inevitable with a greatly increased risk of developing comorbid psychiatric illness such as depression.

Available drug treatments for chronic pain conditions are subject to various limitations. Non-steroidal anti-inflammatory drugs such as ibuprofen and aspirin and opiates such as morphine, can be effective at treating chronic pain with a predominant inflammatory component, but are much less effective against chronic pain disorders associated with nerve damage (neuropathic pain). In addition the pain relief that can be obtained with opiates is often associated with tolerance and dependence, with increased risk of developing undesirable side effects.

Numerous random-controlled trials have shown that drugs capable of modulating monoamine transmission within the CNS such as the tricyclic antidepressant amitriptyline, are effective in the treatment of chronic pain. Whilst it is likely that inhibition of both noradrenaline and serotonin uptake within specific brainstem and forebrain areas is required to obtain analgesic efficacy, it has recently been reported that injection of a specific dopamine reuptake inhibitor into the forebrain can also inhibit the processing of pain (Burkey, A. R. et al.; J. Neurosci. (1999) 19 (10) 4169-4179).

Thus, although some chronic pain conditions are relatively well treated at present, significant unmet needs remain. There is a continued requirement to develop more selective and effective therapies that are better tolerated, for the treatment of patients with chronic pain conditions.

DETAILED DISCLOSURE OF THE INVENTION

It has now been found that a triple monoamine reuptake inhibitor is useful in the treatment, prevention or alleviation of chronic pain.

Thus, in a first aspect the invention provides the use of a triple monoamine reuptake inhibitor or a pharmaceutically acceptable salt thereof for the manufacture of a medicament for the treatment, prevention or alleviation of chronic pain.

In a second aspect, the invention provides a method for the treatment, prevention or alleviation of chronic pain in a subject, comprising administering to said subject a therapeutically effective amount of a triple monoamine reuptake inhibitor or a pharmaceutically acceptable salt thereof.

In one embodiment, the triple monoamine reuptake inhibitor is a tropane derivative.

In a further embodiment, the triple monoamine reuptake inhibitor is a compound of the general formula I

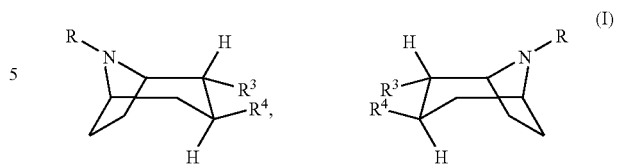

or a pharmaceutically acceptable addition salt thereof or the N-oxide thereof, wherein R is hydrogen, alkyl, alkenyl, alkynyl, cycloalkyl, cycloalkylalkyl or 2-hydroxyethyl;

$R^3$ is $CH_2$—X—R',
  wherein X is O, S, or NR";
wherein R" is hydrogen or alkyl; and
R' is alkyl, alkenyl, alkynyl, cycloalkyl, cycloalkylalkyl, or —CO-alkyl;

$R^4$ is
  3,4-methylenedioxyphenyl or
  phenyl, benzyl, naphthyl, or heteroaryl, each of which may be substituted one or more times with substituents selected from the group consisting of halogen, $CF_3$, CN, alkoxy, cycloalkoxy, alkyl, cycloalkyl, alkenyl, alkynyl, amino, nitro, heteroaryl, and aryl.

In a still further embodiment, the triple monoamine reuptake inhibitor is a 2,3-trans di-substituted tropane compound of the general formula I. In a further embodiment, the triple monoamine reuptake inhibitor is a (1R,2R,3S)-2,3-trans di-substituted tropane compound of the general formula I.

In a still further embodiment, R is hydrogen or alkyl. In a special embodiment, R is hydrogen. In a further embodiment, R is alkyl, such as methyl.

In a further embodiment, $R^3$ is $CH_2$—X—R', wherein X is O or S, and R' is alkyl, cycloalkyl or cycloalkylalkyl. In a special embodiment, $R^3$ is $CH_2$—O—R', wherein R' is alkyl, cycloalkyl or cycloalkylalkyl. In a special embodiment, R' is methyl, ethyl, isopropyl, or cyclopropylmethyl. In a further embodiment, R' is methyl or ethyl.

In a further embodiment of the compound of general formula I, $R^4$ is phenyl, which may be substituted one or more times with substituents selected from the group consisting of halogen, $CF_3$, CN, alkoxy, cycloalkoxy, alkyl, cycloalkyl, alkenyl, alkynyl, amino, nitro, and heteroaryl. In a still further embodiment, $R^4$ is phenyl, which may be substituted one or more times with substituents selected from the group consisting of halogen, $CF_3$, and CN. In a special embodiment, $R^4$ is phenyl substituted once or twice with halogen, such as chlorine. In a further embodiment, $R^4$ is 4-chlorophenyl. In a still further embodiment, $R^4$ is 3,4-dichlorophenyl.

In a still further embodiment, the triple monoamine reuptake inhibitor is a 2,3-trans disubstituted tropane compound of general formula I wherein R is hydrogen, methyl, ethyl or propyl;
$R^3$ is —$CH_2$—X—R', wherein X is O or S, and R' is methyl, ethyl, propyl, or cyclopropylmethyl; and
$R^4$ is phenyl, which may be substituted one or more times with substituents selected from the group consisting of halogen, $CF_3$, and CN.

In a further embodiment, the triple monoamine reuptake inhibitor is a 2,3-trans disubstituted tropane compound of general formula I wherein R is hydrogen or methyl;
$R^3$ is —$CH_2$—O—R', wherein R' is methyl, ethyl, propyl, or cyclopropylmethyl; and R[4] is phenyl, which may be substituted one or more times with halogen.

In a still further embodiment, the triple monoamine reuptake inhibitor is a 2,3-trans disubstituted tropane compound of general formula I wherein
R is hydrogen or methyl;
R[3] is —CH$_2$—O—R', wherein R' is methyl or ethyl; and
R[4] is 4-chlorophenyl or 3,4-dichlorophenyl.

In a special embodiment, the tropane derivative having dopamine reuptake inhibitor activity is a compound of the general formula (I) selected from:
(1R,2R,3S)-2-Methoxymethyl-3-(3,4-dichlorophenyl)-tropane;
(1R,2R,3S)-2-Isopropoxymethyl-3-(3,4-dichlorophenyl)-tropane;
(1R,2R,3S)-2-Ethoxymethyl-3-(3,4-dichlorophenyl)-tropane;
(1R,2R,3S)-2-Cyclopropylmethyloxymethyl-3-(3,4-dichlorophenyl)-tropane;
(1R,2R,3S)-2-Methoxymethyl-3-(4-chlorophenyl)-tropane;
(1R,2R,3S)-N-Normethyl-2-methoxymethyl-3-(4-chlorophenyl)-tropane;
(1R,2R,3S)-2-Ethoxymethyl-3-(4-chlorophenyl)-tropane;
(1R,2R,3S)-N-Normethyl-2-methoxymethyl-3-(3,4-dichlorophenyl)-tropane;
(1R,2R,3S)-N-Normethyl-2-ethoxymethyl-3-(3,4-dichlorophenyl)-tropane;
(1R,2R,3S)-N-Normethyl-2-ethoxymethyl-3-(4-chlorophenyl)-tropane;
(1R,2R,3S)-N-Normethyl-2-cyclopropylmethyloxymethyl-3-(4-chlorophenyl)-tropane;
(1R,2R,3S)-2-Cyclopropylmethyloxymethyl-3-(4-chlorophenyl)-tropane;
(1R,2R,3S)-2-Ethylthiomethyl-3-(3,4-dichlorophenyl)-tropane;
(1R,2R,3S)-2-Hydroxymethyl-3-(4-fluorophenyl)tropane;
(1R,2R,3S)-2-Hydroxymethyl-3-(3,4-dichlorophenyl)tropane;
(1R,2R,3S)-2-Hydroxymethyl-3-(4-chlorophenyl)tropane;

or a pharmaceutically acceptable addition salt thereof.

In a further embodiment, the chronic pain is inflammatory pain, neuropathic pain, fibromyalgia, chronic fatigue syndrome, tension-type headache or any pain arising as a consequence of or associated with depressive illness. In a special embodiment, the chronic pain is inflammatory pain. In a further embodiment, the chronic pain is neuropathic pain. In a still further embodiment, the chronic pain is fibromyalgia. In a further embodiment, the chronic pain is chronic fatigue syndrome. In a still further embodiment, the chronic pain is tension-type headache. In a further embodiment, the chronic pain is any pain arising as a consequence of or associated with depressive illness.

Triple Monoamine Reuptake Inhibitor

A triple monoamine reuptake inhibitor is a compound that inhibits the reuptake of the three monoamines serotonin, noradrenaline, and dopamine.

The potential of a given substance to act as a triple monoamine dopamine reuptake inhibitors activity may be determined using standard in vitro binding assays and/or standard in vivo functionality tests.

The triple monoamine reuptake inhibitors for use according to the invention may in particular be tropane derivatives such as those disclosed in WO 97/30997 (NeuroSearch A/S).

In one embodiment, the triple monoamine reuptake inhibitor shows $IC_{50}$ values of less than 100 nM, preferably less than 50 nM, and more preferably less than 10 nM for each of the monoamines dopamine, serotonin, and noradrenaline when tested for in vitro inhibition according to standard test methods.

In a second embodiment, the triple monoamine reuptake inhibitor shows $ED_{50}$ value of less than 50 mg/kg, preferably less than 10 mg/kg, more preferably less than 5 mg/kg for each of the monoamines dopamine, serotonin, and noradrenaline when tested for in vivo inhibition according to standard test methods.

The above examples of triple monoamine reuptake inhibitors are not intended to be in any way limiting to the scope of the invention as claimed.

Chronic Pain Conditions

In the context of the present invention, the term "chronic pain" includes inflammatory pain, neuropathic pain, fibromyalgia, chronic fatigue syndrome, chronic tension-type headache, and any pain arising as a consequence of or associated with depressive illness.

Inflammatory pain includes without limitation, osteoarthritis, rheumatoid arthritis, back pain, cancer pain, irritable bowel pain, post-operative pain, pain associated with viral infection or diseases with a recognised peripheral or central inflammatory component.

Neuropathic pain includes without limitation, pain arising from any disease state causing damage to the peripheral or central nervous systems, back pain, cancer pain, chemotherapy induced neuropathy, irritable bowel pain, post-stroke pain, post-operative pain, sympathetically-maintained pain, phantom-limb pain, pain associated with viral infection such as postherpetic neuralgia, trigeminal neuralgia, dental pain, myofacial pain, diabetic neuropathy, pain associated with autoimmune disease such as HIV infection and multiple sclerosis, phantom-limb pain, arthritis, or drug-induced neuropathy.

Definition of Substituents

In the context of this invention alkyl designates a straight chain or a branched chain containing of from one to six carbon atoms ($C_1$-$C_6$ alkyl), including but not limited to methyl, ethyl, propyl, isopropyl, butyl, isobutyl, t-butyl, pentyl and hexyl. In a preferred embodiment of this invention alkyl represents a $C_1$-$C_4$ alkyl, preferably a $C_1$-$C_3$ alkyl, most preferred methyl, ethyl, propyl or isopropyl.

In the context of this invention cycloalkyl designates a cyclic alkyl containing of from three to seven carbon atoms ($C_3$-$C_7$ cycloalkyl), including but not limited to cyclopropyl, cyclobutyl, cyclopentyl, and cyclohexyl.

In the context of this invention alkenyl designates a group containing of from two to six carbon atoms ($C_2$-$C_6$ alkenyl), including at least one double bond, for example, but not limited to ethenyl, 1,2- or 2,3-propenyl, 1,2-, 2,3-, or 3,4-butenyl.

In the context of this invention alkynyl designates a group containing of from two to six carbon atoms ($C_2$-$C_6$ alkynyl), including at least one triple bond, for example, but not limited to ethynyl, 1,2- or 2,3-propynyl, 1,2-, 2,3- or 3,4-butynyl.

In the context of this invention cycloalkylalkyl designates a cycloalkyl as defined above which is attached to an alkyl as also defined above, e.g. cyclopropylmethyl.

In the context of this invention aryl designates an aromatic hydrocarbon, such as phenyl or naphthyl.

In the context of this invention alkoxy designates an alkyl-O—, where alkyl is as defined above.

In the context of this invention halogen designates a fluorine, a chlorine, a bromine or an iodine atom.

In the context of this invention amino represents $NH_2$, NH-alkyl, or N-(alkyl)$_2$, wherein alkyl is as defined above.

In the context of this invention heteroaryl designates a 5- or 6-membered heterocyclic monocyclic group, for example, but not limited to, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol-4-yl, 2-imidazolyl, 4-imidazolyl, 5-imidazolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, and 4-pyrazolyl.

Steric Isomers

The chemical compounds for use in the invention may exist in (+) and (−) forms as well as in racemic forms. The use of racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds for use in the invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Moreover, some of the chemical compounds for use in the invention may thus exist in two forms, syn- and anti-form (Z- and E-form), depending on the arrangement of the substituents around a —C=C— or —C=N— double bond. A chemical compound for use according to the present invention may thus be the syn- or the anti-form (Z- and E-form), or it may be a mixture hereof.

Pharmaceutically Acceptable Salts

The triple monoamine reuptake inhibitor for use according to the invention may be provided in any form suitable for the intended administration. Suitable forms include pharmaceutically (i.e. physiologically) acceptable salts, and pre- or prodrug forms of the chemical compound for use according to the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Metal salts of a chemical compound for use according to the invention include alkali metal salts such as the sodium salt of the chemical compound containing a carboxy group.

The term "prodrug" denotes a compound, which is a drug precursor and which, following administration and absorption, release the drug in vivo via some metabolic process.

Particularly favoured prodrugs are those that increase the bioavailability of the compounds for use according to the invention (e.g. by allowing an orally administrered compound to be more readily absorbed into the blood) or which enhance delivery of the parent compound to a specific biological compartment (e.g. the brain or lymphatic system).

Thus examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

Pharmaceutical Compositions

The invention provides the use of pharmaceutical compositions comprising a therapeutically effective amount of the triple monoamine reuptake inhibitor. While a triple monoamine reuptake inhibitor for use in therapy according to the invention may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the triple monoamine reuptake inhibitor, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

Pharmaceutical compositions for use according to the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound for use according to the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound for use according to the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound for use according to the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound for use according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouth-washes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

Methods of Therapy

In another aspect the invention provides method for the treatment, prevention or alleviation of chronic pain in a subject, comprising administering to said subject a therapeutically effective amount of a triple monoamine reuptake inhibitor or a pharmaceutically acceptable salt thereof.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Preparation

The compounds of general formula (I) for use in the invention may be prepared by conventional methods of chemical synthesis, e.g. those described WO 97/30997 (NeuroSearch A/S).

The starting materials for the processes described in the present application are known or may readily be prepared by conventional methods from commercially available chemicals.

The end products of the reactions described herein may be isolated by conventional techniques, e.g. by extraction, crystallisation, distillation, chromatography, etc.

Any possible combination of two or more of the embodiments described in this patent application is comprised within the scope of the present invention.

The invention claimed is:

1. A method for the treatment or alleviation of a chronic pain condition in a subject comprising:
    administering to said subject a therapeutically effective amount of a triple monoamine reuptake inhibitor wherein the triple monoamine reuptake inhibitor is a compound of formula (I)

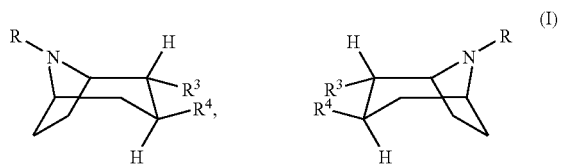

or a pharmaceutically acceptable addition salt thereof or the N-oxide thereof,
wherein the chronic pain condition is selected from at least one of the group of chronic pain conditions consisting of: inflammatory pain, neuropathic pain, fibromyalgia and tension-type headache, and
wherein
R is hydrogen or methyl;
$R^3$ is —$CH_2$—O—R', wherein R' is methyl, ethyl or propyl; and
$R^4$ is 3,4-dichlorophenyl.

2. The method according to claim 1, wherein the tropane derivative is selected from
    (1R,2R,3S)-2-Methoxymethyl-3-(3,4-dichlorophenyl)-tropane;
    (1R,2R,3S)-2-Isopropoxymethyl-3-(3,4-dichlorophenyl)-tropane;
    (1R,2R,3S)-2-Ethoxymethyl-3-(3,4-dichlorophenyl)-tropane;
    (1R,2R,3S)-N-Normethyl-2-methoxymethyl-3-(3,4-dichlorophenyl)-tropane;
    (1R,2R,3S)-N-Normethyl-2-ethoxymethyl-3-(3,4-dichlorophenyl)-tropane;
    or a pharmaceutically acceptable addition salt thereof.

3. The method according to claim 1, wherein R' is ethyl.

4. The method according to claim 1, wherein the tropane derivative is selected from:
    (1R,2R,3S)-2-Ethoxymethyl-3-(3,4-dichlorophenyl)-tropane;
    (1R,2R,3S)-N-Normethyl-2-ethoxymethyl-3-(3,4-dichlorophenyl)-tropane;
    or a pharmaceutically acceptable addition salt thereof.

5. A method for the treatment or alleviation of a chronic pain condition in a subject comprising:
    administering to said subject a therapeutically effective amount of (1R,2R,3S)-2-Ethoxymethyl-3-(3,4-dichlorophenyl)-tropane;
    or a pharmaceutically acceptable addition salt thereof,
    wherein the chronic pain condition is selected from at least one of the group of chronic pain conditions consisting of: inflammatory pain, neuropathic pain, fibromyalgia and tension-type headache.

6. A method for the treatment or alleviation of a chronic pain condition in a subject comprising:
    administering to said subject a therapeutically effective amount of
    (1R,2R,3S)-N-Normethyl-2-methoxymethyl-3-(3,4-dichlorophenyl)-tropane;
    or a pharmaceutically acceptable addition salt thereof,
    wherein the chronic pain condition is selected from at least one of the group of chronic pain conditions consisting of: inflammatory pain, neuropathic pain, fibromyalgia and tension-type headache.

* * * * *